United States Patent [19]
Ikeuchi et al.

[11] Patent Number: 5,679,645
[45] Date of Patent: Oct. 21, 1997

[54] SIALIC ACID POWDER AND PROCESS FOR THE PREPARATION THEREOF

[75] Inventors: Yoshihiro Ikeuchi, Sayama; Takafumi Yakabe, Kawagoe, both of Japan

[73] Assignee: Snow Brand Milk Products Co., Ltd., Japan

[21] Appl. No.: 357,377

[22] Filed: Dec. 16, 1994

[30] Foreign Application Priority Data

Jul. 23, 1993 [JP] Japan .................................. 5-202586

[51] Int. Cl.$^6$ .............................. A61K 31/70; C07H 1/00
[52] U.S. Cl. .................. 514/42; 536/17.2; 536/18.5; 536/124; 536/127
[58] Field of Search ............................. 536/17.2, 18.2, 536/18.5, 123.1, 124, 127; 514/42

[56] References Cited

U.S. PATENT DOCUMENTS

| | | | |
|---|---|---|---|
| 4,002,748 | 1/1977 | Bornstein et al. | 424/246 |
| 4,042,576 | 8/1977 | Eustache | 260/112 R |
| 4,526,727 | 7/1985 | Petty | 260/465 D |
| 5,118,516 | 6/1992 | Shimatani et al. | 426/271 |

FOREIGN PATENT DOCUMENTS

| | | |
|---|---|---|
| 307559 | 3/1989 | European Pat. Off. . |
| 0 474 410 A2 | 3/1992 | European Pat. Off. ......... C07H 13/04 |
| 61-243096 | 10/1986 | Japan . |
| 63-044586 | 2/1988 | Japan . |
| 01163110 | 6/1989 | Japan . |
| 01163112 | 6/1989 | Japan . |
| 01163114 | 6/1989 | Japan . |
| 03251593 | 11/1991 | Japan . |
| 03262495 | 11/1991 | Japan . |
| 05244976 | 9/1993 | Japan . |
| 06256195 | 9/1994 | Japan . |

*Primary Examiner*—John Kight
*Assistant Examiner*—Howard C. Lee
*Attorney, Agent, or Firm*—Testa, Hurwitz & Thibeault, LLP

[57] ABSTRACT

An amorphous sialic acid powder is disclosed. It is prepared by rapidly freezing an aqueous solution of sialic acids and freeze-drying the frozen product. It has a melting point of 131°–136° C. (decomposed) and exhibits no peaks inherent to crystals in differential scanning thermal analysis (at 165°–200° C.) and X-ray diffractiometric pattern (in the range of $5° \leq 2\theta \leq 40°$). The amorphous sialic acid powder is highly reactive and can be used as a raw material for drugs and the like.

4 Claims, 5 Drawing Sheets

SIALIC ACID POWDER AND PROCESS FOR THE PREPARATION THEREOF

BACKGROUND OF THE INVENTION

1. Field of the Invention

The present invention relates to a new amorphous sialic acid powder and a process for preparing the same. The sialic acid powder of the present invention can be prepared by rapidly freezing a sialic acid solution and freeze-drying the frozen matter.

2. Description of Background Art

Sialic acids are acidic carbohydrates normally found in non-reducing terminals of sugar chains of complex carbohydrates. The structural frame is N-acetyl or N-glycolyl derivatives of neuraminic acid. Besides these, more than ten species of sialic acids having one to several 0-acetylated hydroxy groups in the structural frame have been discovered. "Sialic acid" is deemed to be a generic name of these derivatives (e.g. Roland Schauer, Biochemistry, 59 (3), 133–146 (1987)).

Complex carbohydrates, such as glycoproteins or glycolipids, are known as sialic acid-containing compounds. These compounds are known to play an important role in intercellular recognition, biophylaxis mechanism, and foreign matter recognition owing to the bonding of sialic acid to sugar chains. Further, sialic acids are known to possess a receptor activity of influenza virus and the activity of controlling the in-blood half life of sugar chain-containing blood components. Numerous studies concerning sialic acids have been ongoing in recent years. In addition, sialic acids themselves are known to have an expectorant action. Use of sialic acids as a drug was also investigated (Japanese Patent Application Laid-open (kokai) 127484/1986).

Besides these naturally occurring sialic acid-containing compounds, a great deal of attention has been given to unnatural-type, synthetic sialic acid/containing compounds. Functions exhibited by sialic acids when they are bonded to sugar chains, such as masking of the compounds from biophylaxis mechanism or extension of in vivo half life, have led researchers to make various trials, such as reduction of a dosage, alleviation of toxicity, and the like, by artificially incorporating sialic acid in drugs. Further, the knowledge that sialic acid-containing sugar chains function as receptors of certain influenza viruses leads to a reverse application of this function. That is to say, some researchers are motivated to use sialic acid derivatives as a factor of infection prevention by synthesizing analogs of these receptors and attaching viruses to the analogs to prevent infections. In view of the development on the researches concerning sialic acid derivatives, demand has increased for sialic acids among manufacturers, inter alia among pharmaceutical manufacturers, as a starting material of organic synthesis or enzymatic synthesis. Furthermore, the use of sialic acids as a food material can be expected in view of the expectorant action and the infection preventing effect of sialic acids, when the characteristics of the sialic acids or the process for converting them to derivatives meets with the standard of food applications.

In the past, sialic acids were obtained mainly from acidic hydrolyzed products of nests of edible birds. In order to satisfy the demands of sialic acids at industrial scale, methods for preparing sialic acids from various materials have been reported in recent years. Besides the method of purifying natural raw materials such as nests of edible birds, eggs, and milks (Japanese Patent Application Laid-open (kokai) No. 28411/1988), a method of purifying from colominic acid produced by E. coli mutant is used. Another method is synthesizing sialic acids from N-acetylglucosamine and sodium pyruvate by the reverse reaction of sialic acid aldolase which can be available in a large amount owing to the recent development of gene manipulation technique. In any methods, it is a necessary process to make the sialic acids into powder and dry the powder. Conventionally, the main method has been to crystallize sialic acids from a water-organic solvent system and then dry the crystals. According to the reports heretofore surfaced, it is a typical method to crystallize sialic acids by adding acetic acid as a poor dissolving sovent, collect the produced crystals, and dry them. The properties of sialic acid needles without crystal water obtained by this method are generally recognized as the properties of sialic acids. However, in this method explosion-proofing and rust-proofing treatments are required in all equipments such as crystal filters, mother liquid condensers, and crystal dryers due to the use of a large amount of acetic acid. Furthermore, acetic acid odor must be removed from the final products, but it is very difficult.

Ogura et al. discovered that prisms containing two mols of crystal water can be obtained by recrystallizing sialic acids from a water-dioxane system (Chem. Lett, 1003–1006 (1984)). The prisms can be used as food when an organic solvent applicable to food is used as a poor dissolving solvent instead of dioxane. However, because the crystals contain water in an amount of 10.43% of the molecule, these are not suitable as a starting material for the synthesis of organic compounds for which the reactions are carried out under conditions where the presence of water is forbidden.

Furthermore, although a method of drying sialic acid solutions by freeze-dry is known, there have been no studies concerning the correlation between the rate of freeze-dry of the sialic acid solution and the solid properties of the resulting sialic acid powder, including the degree of crystallization. The final product consists of a mixture of an amorphous portion and dihydrate prisms. It is very difficult to homogenize properties of the solid and value of water contained therein. The subjects of the present invention are therefore to provide a process for preparing sialic acids without treatment using acetic acid and to provide sialic acid powder with homogeneous properties of the solid, water content, and the like.

The present inventor has undertaken detailed studies on the solid properties of needles and dihydrate prisms of sialic acid, which are typical examples of sialic acid powders, and the solid properties of freeze-dried powders of sialic acids prepared under various conditions. As a result, the present inventor has found that a complete amorphous sialic acid powder can be obtained by rapidly freezing an aqueous solution of sialic acids so as to prevent formation of any crystal structures, and then freeze-drying the frozen product. This finding has led to the completion of the present invention.

SUMMARY OF THE INVENTION

Accordingly, an object of the present invention is to provide an amorphous sialic acid powder.

Another object of the present invention is to provide a sialic acid powder having the following properties, (a) broad absorption by differential scanning thermal analysis in the range of from 165° C. to 200° C. (see FIG. 1) with no clear heat absorption peaks in this temperature range, (b) a melting point of 13°–136° C. (decomposition temperature) in a melting point measurement (direct observation without correction), and (c) a broad scanning angle (2θ) of 5°–40°, with no clear peaks, in an X-ray diffractiometric pattern (see FIG. 5).

Still another object of the present invention is to provide a process for preparing an amorphous sialic acid powder comprising rapidly freezing an aqueous solution of sialic acids and freeze-drying the frozen product.

Other objects, features and advantages of the invention will hereinafter become more readily apparent from the following description.

DETAILED DESCRIPTION OF THE INVENTION AND PREFERRED EMBODIMENTS

Figure 1:
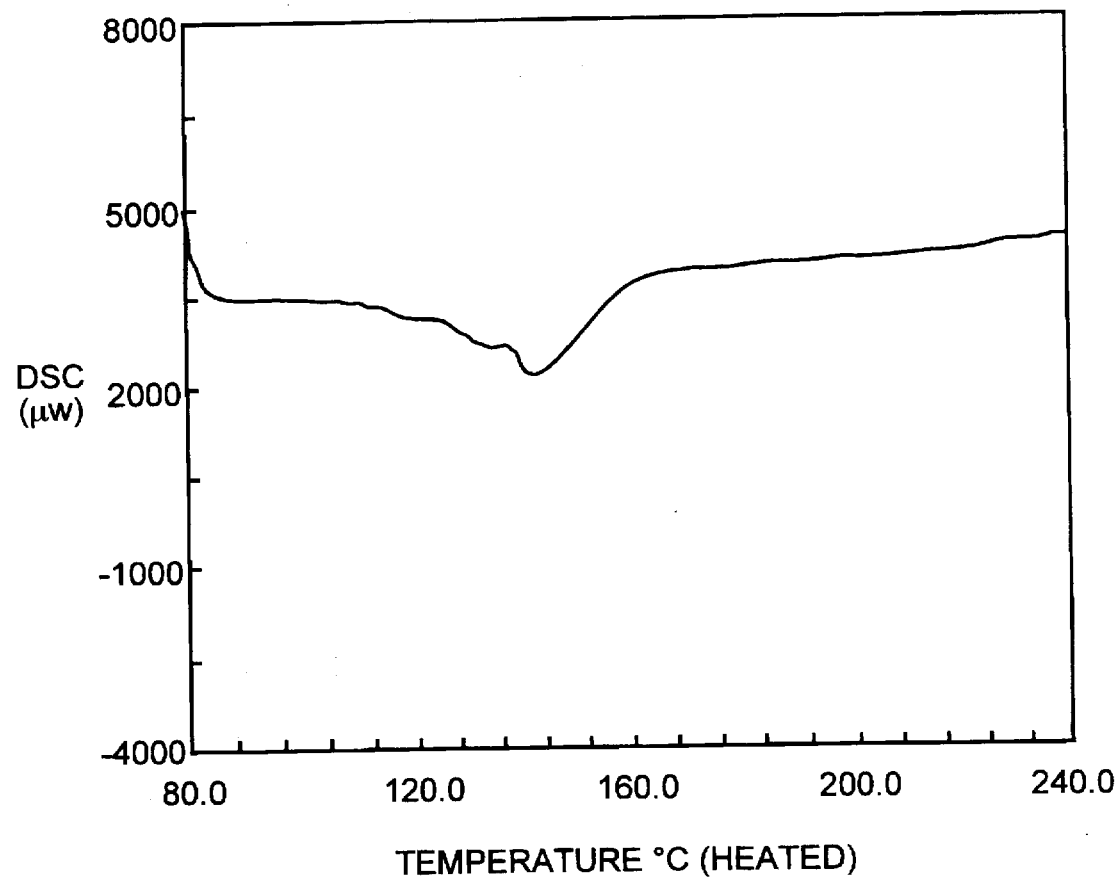
FIG. 1 is a graph obtained by the differential scanning thermal analysis of the amorphous sialic acid powder (Amorphous Powder 1—1) prepared in Example 1.

The amorphous sialic acid powder of the present invention can be prepared by rapidly freezing an aqueous solution of sialic acids so as to prevent formation of any crystal structures, and then freeze-drying the frozen product.

Investigations in the physical and chemical characteristics of the sialic acid powder produced by the process of the present invention revealed that not only it can be used for organic chemical reactions under the conditions where the presence of water is forbidden in quite the same manner as the conventionally known sialic acid needles, but also it can exhibit superiority to such sialic acid needles, in terms of solubility in organic solvents and the reactivity, due to its amorphous properties. Further, the sialic acid powder of the present invention was found to be more excellent in its solubility in water than both the needles and the prisms.

There are no specific limitations to the raw materials and the process for producing the aqueous solution of sialic acids used in the present invention. Examples include those produced from naturally occurring materials, such as nests of edible birds, eggs, and milks, and purified by known methods. In particular, sialic acids produced from these raw materials can be used as food materials as they are. Besides these raw materials, sialic acids purified from colominic acid obtained from E. coli mutants are acceptable. Sialic acids synthesized in a large amount owing to the recent development of gene manipulation technique from N-acetylglucosamine and sodium pyruvate by the reverse reaction of sialic acid aldolase can be also used. Needless to say, raw materials are not limited to those mentioned above.

The aqueous solution must be frozen as a pre-treatment procedure for the freeze-dry. Conventionally, the freezing was carried out using a freezer at –20° C. or by placing the solution on a shelf provided in a freeze-dryer where cooling is effected by the cooling medium in several hours to overnight.

Homogeneous powders can be produced by these methods in the case where the object material can not be crystallized during the freezing process. However, the present inventor has confirmed that no homogeneous powders can be obtained by these methods in the case of sialic acids of which the crystal may contain dihydrate (Examples 1, 3, and 4). As a result of the investigations by the present inventor based on this finding, partial formation of crystals containing dihydrate was prevented and a complete amorphous freeze-dried powder was successfully produced by rapidly freezing the aqueous solution of sialic acids (Example 5). This complete amorphous freeze-dried powder had an IR spectrum and water content very close to those of needles. The melting point was not clear and lower than needles (Example 2). These are due to extremely rough and irregular alignment of molecules in the solid as compared with those in the crystals. The present inventor has found that these properties assist to increase the solubility and reactivity of the powder, though the amorphous powder and the crystals are the same substance (Example 6).

The present inventor has further found that if the aqueous solution of sialic acids is frozen as slowly as it was conventionally frozen, the sialic acid powder obtained after freeze-dry is a mixture of crystals and amorphous matters. It was difficult to obtain a homogeneous powder. The inventor confirmed that this mixture and the amorphous sialic acid powder of the present invention are clearly distinguished from each other by differential scanning thermal analysis and X-ray diffractiometry (Examples 4 and 5).

There are no specific limitations to the concentration of sialic acids in the aqueous solution used for the freeze-dry. Although a range of 0.1–50% by weight is applied, 10–50% by weight is more preferred in view of the efficiency of the freeze-dry. Here, consideration should be given to the fact that the sialic acids are more easily crystallized at a higher concentration. That is to say, using a solution with a higher sialic acid concentration, homogeneous sialic acid powders can be produced more efficiently with a smaller quantity of water vaporization by selecting quenching conditions under which a high rate of freezing can be achieved.

Although there are no specific limitations to the quenching method, feeding the aqueous solution of sialic acids in portions to a vessel cooled with liquid nitrogen, a dry ice-acetone bath, or a dry ice-ethanol bath is more preferred than feeding the all amount at one time. It is important to select a quenching method and a freezing rate which can effectively prevent the frozen sialic acids from forming a crystal structure. It is desirable to complete the freezing at a temperature below –20° C. in 0.01–900 seconds, preferably in 0.01–60 seconds.

In this manner, crystallization of sialic acid molecules in an aqueous solution can be completely prevented by rapidly freezing the sialic acid aqueous solution, resulting in homogeneity in the solid properties of the powder obtained by the succeeding freeze-drying procedure. Further, the sialic acid powder has added advantages over the commercially available sialic acid crystals in terms of solubility and reactivity.

Moreover, as it is not necessary to use a solvent to prepare sialic acid powder in the present invention, there are no risks of impairing health of workers and of occurrence of explosions in the plant. Thus, no investment for explosion-proof is required, which contributes to significant reduction of the production cost. In addition, absence of toxic organic solvents makes it possible for the final product to be used as a food material as they are, if raw materials from natural sources are used for the production of sialic acids.

Other features of the invention will become apparent in the course of the following description of the examples. It is understood that these are given for illustration of the invention and are not intended to be limiting thereof.

EXAMPLES

Example 1

Preparation of Amorphous Sialic Acid Powder 1235 g of an aqueous solution of sialic acids was prepared by dissolving 185.2 g of sialic acids in water. This aqueous solution was charged to a stainless steel bat which was cooled with a sufficient amount of liquid nitrogen at a rate of 100 ml/min and instantaneously frozen. It took 3–15 seconds to freeze the solution completely. This frozen matter of the aqueous solution of sialic acid was subjected to freeze-dry at −25° C. for 4 hours to obtain 184.5 g of amorphous sialic acid powder of the present invention (Amorphous Powder 1-1).

The Amorphous Powder 1-1 thus obtained was pulverized in a mortar and classified to obtain a less than 200 mesh powder.

The period of time required for the solution to be completely frozen was determined from the cryohydrate point measured by inserting an electrode for cryohydrate point measurement in the aqueous solution.

Preparation of control sample.

(1) Preparation of Needles 112 g of an aqueous solution of sialic acids (45%) was prepared by dissolving 50.4 g of sialic acids in water. 700 ml of acetic acid was added and the solution was crystallized overnight at 0° C. Crystals deposited were collected by filtration under reduced pressure, washed with acetone and diethyl ether, and dried overnight at 20° C. under reduced pressure, to obtain 40.1 g of Needles 1-1.

(2) Preparation of Prisms 180 g of an aqueous solution of sialic acids (45%) was prepared by dissolving 80.9 g of sialic acids in water. 70 ml of dioxane was added slowly while stirring and the solution was crystallized overnight at 0° C. Crystals deposited were collected by filtration under reduced pressure, washed with acetone and diethyl ether, and dried overnight at 20° C. under reduced pressure, to obtain 69.5 g of Prisms 1—1.

(3) Preparation of Freeze-dry Powder by Conventional Methods 922 g of an aqueous solution of sialic acids (15%) was prepared by dissolving 138.3 g of sialic acids in water. This solution was divided into two portions, each weighing 461 g. One was frozen by shelf cooler inside a freeze dryer (−40° C.), and the other by a freezer at −20° C. The period of time required for the solution to be frozen was 4.4 hours in the case of the shelf cooler and 6.8 hours in the case of the freezer. Thereafter, each was freeze-dried at 25° C. for 4 days, thus obtaining 68.1 g and 67.5 g of freeze-dried products, respectively. The product prepared by the shelf cooler is called Comparative Powder 1—1, and by the freezer is called Comparative Powder 1-2.

The sialic acid crystals and the powder thus prepared were pulverized in a mortar and classified to obtain a less than 200 mesh powder in the same manner as the Amorphous Powder 1—1 of the present invention.

Example 2

Comparison of Properties

Properties (melting point, IR spectrum) were measured on Amorphous Powder 1-1, Needles 1—1, and Prisms 1—1 prepared in Example 1. The melting points (decomposition point) were measured using a slight quantity melting point analyzer of direct observation-type made by Yanagimoto Co. and the results were recorded without correction. IR spectra were measured by the KBr tablet method. The results are shown in Table 1. As can be seen in Table 1, excepting for the melting point Amorphous Powder 1—1 had the same properties as Needles 1—1, Prisms 1—1, and those of generally recognized as the properties of sialic acid needles in literature (Ogura et al. Chem. Lett, 1003–1005 (1984); "The amino sugars", Academic press, pp 228–229 (1969); etc.).

TABLE 1

Properties of sialic acid powders

| Sample | Water content (%) | m.p. (decomposed) °C. | IR (v/cm, KBr) | | |
|---|---|---|---|---|---|
| | | | COOH | Amide I | Amide II |
| Amorphous Powder 1-1 $C_{11}H_{19}NO_8$ | 2.2 | 131–136 | 1723 | 1652 | 1525 |
| Needles 1-1 $C_{11}H_{19}NO_8$ | 2.1 | 186–189 | 1723 | 1652 | 1525 |
| Prisms 1-1 $C_{11}H_{19}NO_8 \cdot 2H_2O$ | 10.9 | 142–145 | 1755 | 1629 | 1592 |

Example 3

Differential Scanning Thermal Analysis (DSC)

Figure 2:
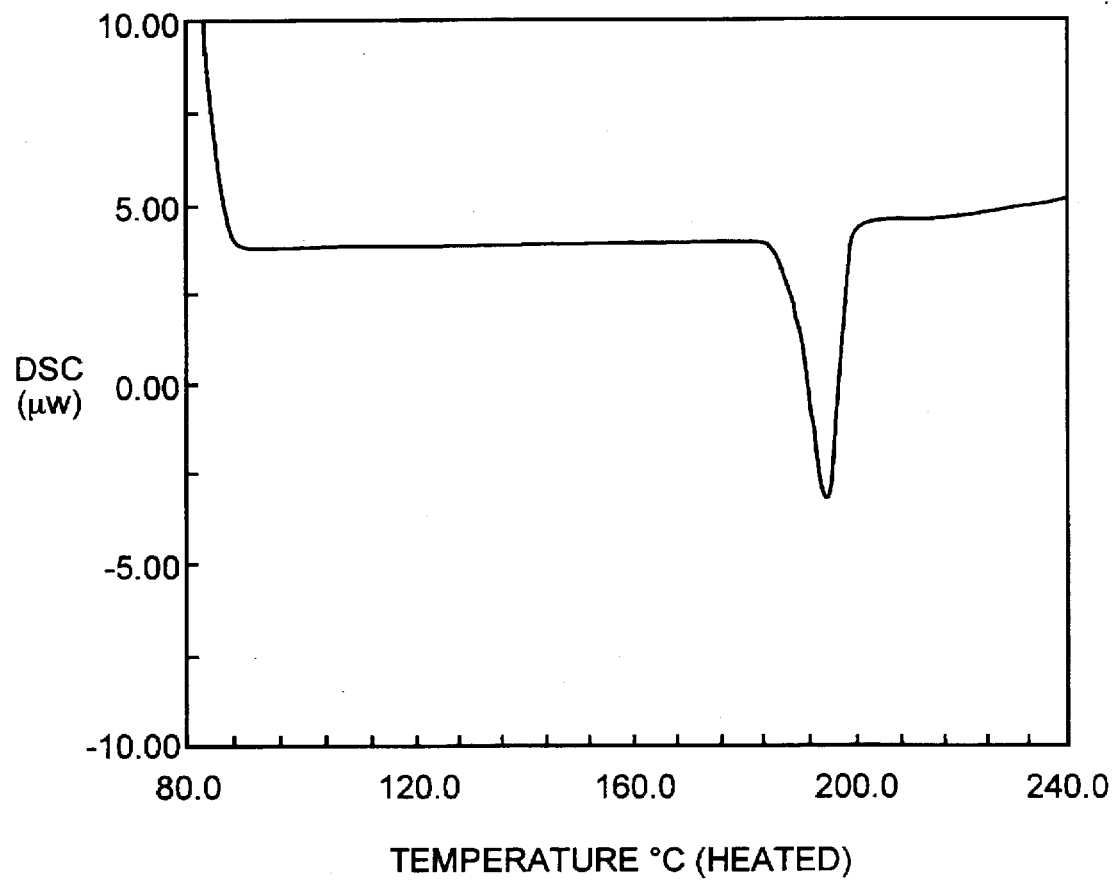
FIG. 2 is a graph obtained by the differential scanning thermal analysis of a sialic acid powder (Comparative Powder 1-2).
Figure 3:
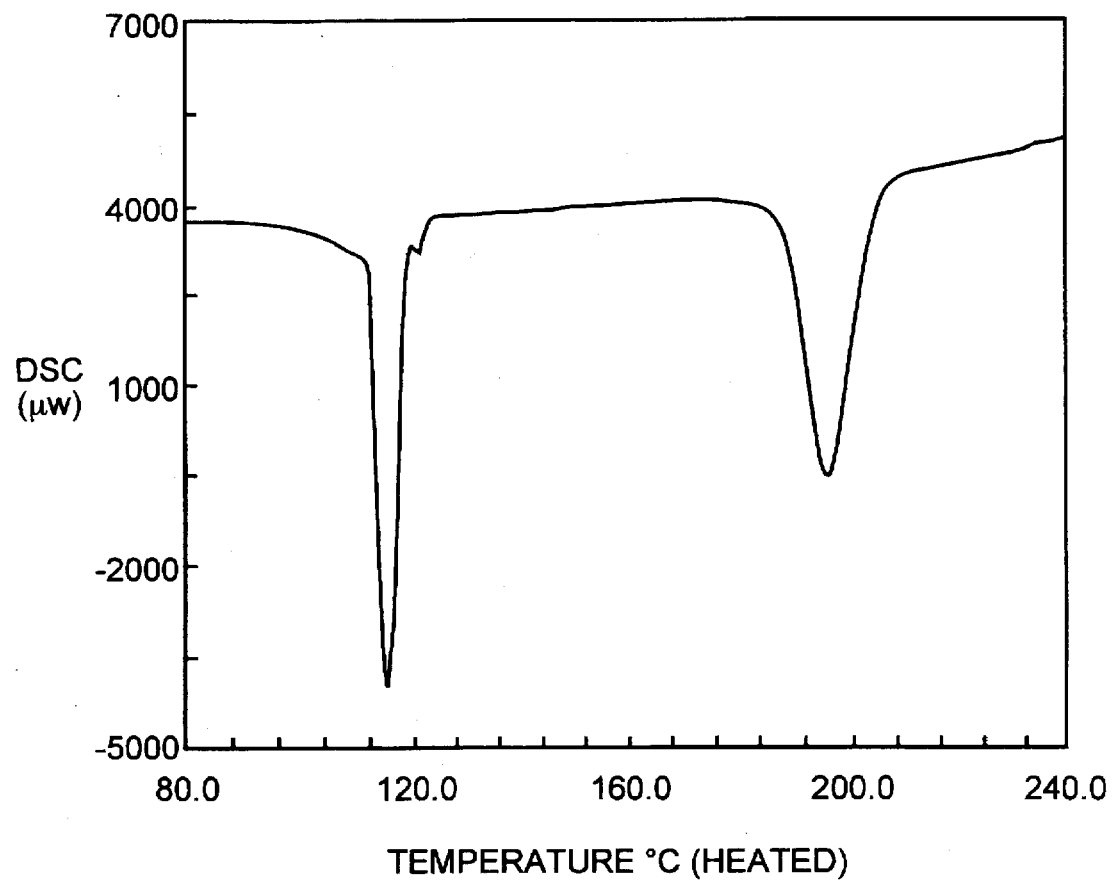
FIG. 3 is a graph obtained by the differential scanning thermal analysis of sialic acid needles (Needles 1—1).

Differential scanning thermal analysis was carried out on Amorphous Powder 1—1, Needles 1—1, and Prisms 1—1 prepared in Example 1 and on Comparative Powder 1-2, using a differential scanning thermal analyzer (DSC200 type, Trademark, manufactured by Seiko Electronic Industry). The results are shown in FIGS. 1–4. As can be seen in these Figures, a single sharp peak was exhibited by Needles 1—1 (FIG. 2). Prisms 1—1 which is a dihydrate showed two sharp peaks, one a peak produced when the crystal water is released and the other when the crystals were decomposed (FIG. 3). Interestingly, Prisms 1—1 were observed to decompose at 142°–145° C. by the direct observation method, but heat absorption peaks due to decomposition were observed both for the needles and the prisms in the range of 165°–200° C. by the DSC measurement.

On the other hand, Amorphous Powder 1—1 of the present invention only exhibited a broad absorption band in the range of 130°–150° C., with no peaks identical to those of the needles and the prisms being observed at all (FIG. 1). The fact too confirmed that Amorphous Powder 1—1 of the present invention is a completely amorphous substance.

Figure 4:
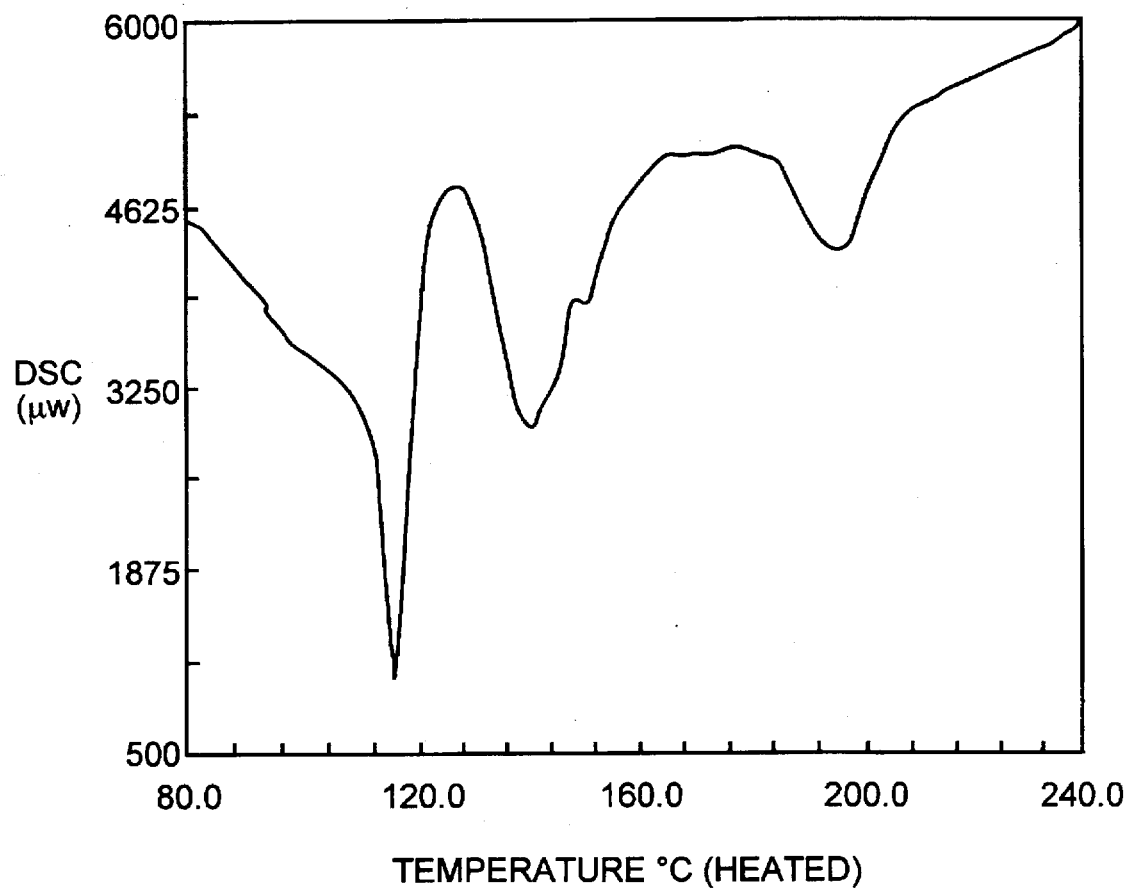
FIG. 4 is a graph obtained by the differential scanning thermal analysis of sialic acid prisms (Prisms 1—1).

In contrast, the Comparative Powder 1-2 exhibited both the two sharp peaks of prisms and a broad absorption band of Amorphous Powder 1—1 (FIG. 4). This indicates that a portion of sialic acid molecules were crystallized into prisms in an aqueous solution when the Comparative Powder 1-2 was frozen in the freezer for 6.8 hours, and after the freeze-drying resulted in a powder in which crystal and amorphous portions were mixed.

As can be understood from these results, it is very important to rapidly freeze an aqueous solution of sialic acids for preparing sialic acid powder by freeze-drying an aqueous solution. The present invention has proven for the first time that it is difficult to obtain a homogeneous product, because partial crystallization of sialic acid takes place and freeze-dried powder changes to a mixture of crystal and amorphous portions, when the aqueous solution is frozen as slowly as it is frozen conventionally.

Furthermore, the present invention has revealed for the first time that confirmation of absence of heat absorption peaks in the range of 165°–200° C. by differential scanning thermal analysis is sufficient for confirming a complete amorphous nature and absolute absence of crystal portions in a freeze-dry sialic acid powder.

Example 4

X-ray Diffractiometric Pattern

X-ray diffractiometric patterns were measured at 40 KV and 20 mA on Amorphous Powder 1—1, Needles 1—1, Prisms 1—1, and Comparative Powder 1-2 prepared in Example 1. Each sample was injected in the range of $5° \leq 2\theta \leq 40°$ and the same conditions such as X-ray intensity, sensitivity, and the like were adopted for all samples. The results are shown in FIG. 5.

Figure 5:
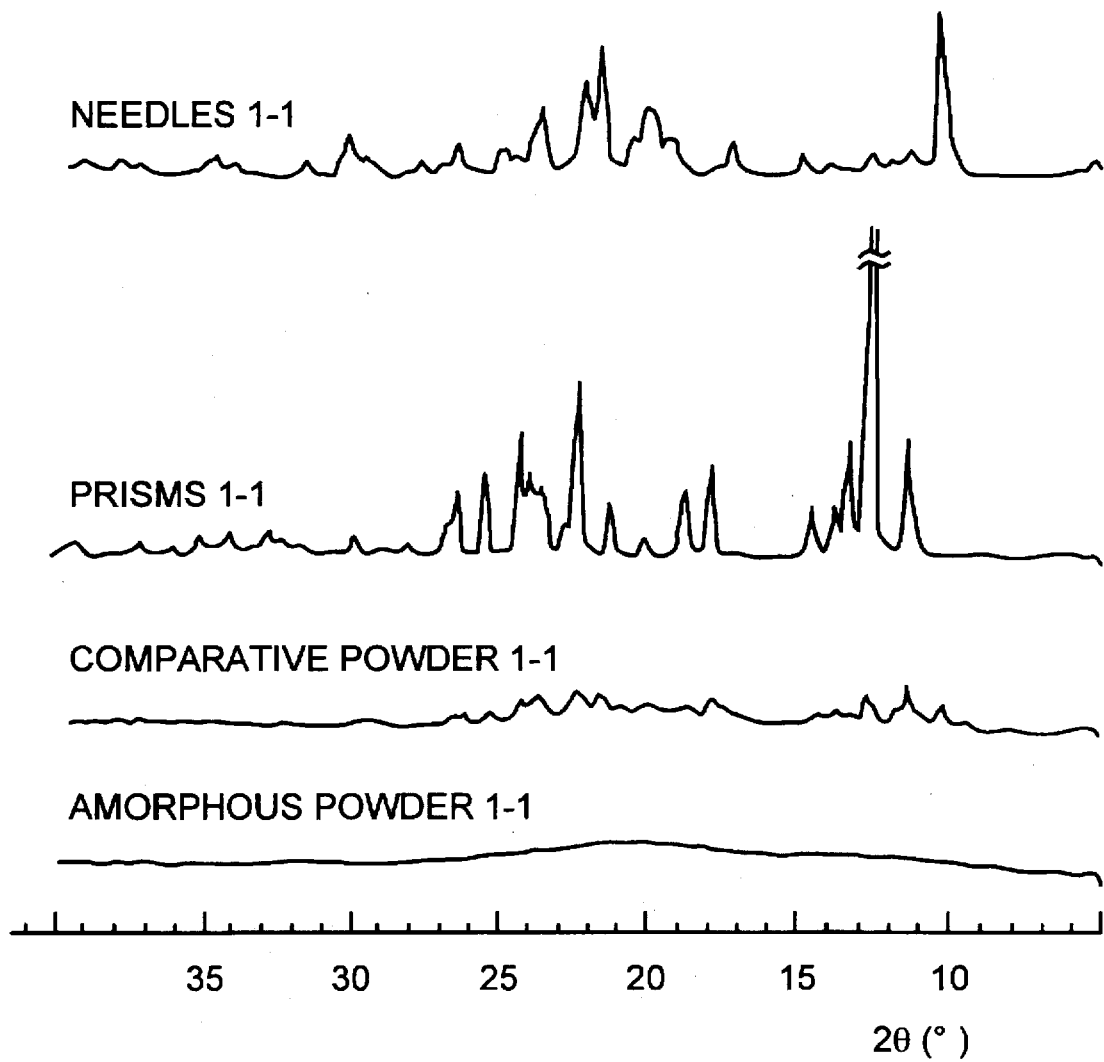
FIG. 5 shows the X-ray diffractiometric pattern of the sialic acid powder prepared in Example 1.

As can be seen in FIG. 5, a number of peaks of sharp and strong scattering lights due to crystal structure were observed in Needles 1—1 and Prisms 1—1, whereas no clear peaks were observed in Amorphous Powder 1—1 of the present invention. This also provided the confirmation that Amorphous Powder 1—1 of the present invention is amorphous containing no crystal portions at all. The same number of far weaker peaks than those in the above two crystals were observed in Comparative Powder 1-2 which were produced by slow freezing. As has been already clarified in Example 3, this is because of the formation of a freeze-dried sialic acid powder in which crystal portions and amorphous portions were mixed, which was caused by the partial crystallization of the sialic acids due to the slow freezing of the solution in a freezer over a long period of time in the process for producing Comparative Powder 1-2 as has been done in the conventional methods.

As explained above, the present invention has revealed for the first time that confirmation of absence of clear scattering light peaks in the range of $5 \leq 2\theta \leq 40°$ by X-ray diffractiometry is sufficient for confirming a complete amorphous nature and absolute absence of crystal portions in a freeze-dry sialic acid powder.

Example 5

Relationship Between the Freezing Rate of a Sialic Acid Aqueous Solution and Properties of the Ultimate Product Relationship between the freezing rate of a sialic acid aqueous solution and properties of the ultimate product was studied. 40% by weight aqueous solution of sialic acids was used and frozen for different periods of time using liquid nitrogen, a cooling shelf, and a freezer, and freeze-dried for 4 days. The degree of crystallization and the water content were measured. The results are given in Table 2.

TABLE 2

Relationship between the freezing rate and the freeze-dried powder

| Time for freezing | Crystallization degree (%) | Water content (%) |
|---|---|---|
| 1 minute or shorter | 0 | 1.1–1.7 |
| 5 minute or shorter | >0.1 | 1.2–1.9 |

TABLE 2-continued

Relationship between the freezing rate and the freeze-dried powder

| Time for freezing | Crystallization degree (%) | Water content (%) |
|---|---|---|
| 10 minute or shorter | 0.2–0.4 | 1.4–2.1 |
| 30 minute or shorter | 1.8–2.3 | 2.4–3.6 |
| 1 hour or shorter | 9.8–15.1 | 3.9–4.8 |
| 3 hours or shorter | 26–35 | 5.1–6.2 |

The results of Table 2 indicate that the longer the time required for freezing, the more crystal portions were produced and the greater was the water content due to increase of the crystal water.

Example 6

Comparison of the Solubility and Reactivity of Sialic Acid Powder

The relationship between the solubility and the reactivity of sialic acid powder was investigated.

Methyl esterification by Fisher method (Ogura et al. Chem. Pharm. Bull., 34, 1479 (1986)) was carried out as a typical reaction in an organic solvent.

A suspension of 10 g of Dowex 50 (trademark, manufactured by Dow Chemical; H+-type, 100–200 mesh, washed with hot methanol) in 100 ml of methanol was prepared. 10 g of Amorphous Powder 1—1, Needles 1—1, or Prisms 1—1 prepared in Example 1 was each charged to the suspension at 25° C. while vigorously stirring. While continuing the stirring at 25° C., the mixture was sampled from time to time to measure the time required for the sialic acids to be dissolved completely to form a clear solution, the degree of reaction, and the final reaction yield. The reaction yield was calculated by HPLC (HPX-87H column, trademark, manufactured by Bio Rad Co.). The results are shown in Table 3

TABLE 3

Solubility and Reactivity of Various Sialic Acid Powders

| Sample | Time required for complete dissolution | Reaction yield after 2 hours | Reaction yield after 5 hours |
|---|---|---|---|
| Amorphous Powder 1-1 | 6 minutes | 100% | 100% |
| Needles 1-1 | 27 minutes | 78% | 100% |
| Prisms 1-1 | Was not completely dissolved | 57% | 79% |

As can be seen from Table 3, Amorphous Powder 1—1 of the present invention was dissolved fastest and completed the reaction in a shortest period of time. Prisms 1—1 did not completely dissolved after 5 hours, and 100% of reaction was not achieved even after the reaction of 24 hours. This is considered that the esterification reaction was terminated due to the crystal water contained in an amount of about 10% in the powder.

Obviously, numerous modifications and variations of the present invention are possible in light of the above teachings. It is therefore to be understood that within the scope of the appended claims, the invention may be practiced otherwise than as specifically described herein.

What is claimed is:

1. A composition comprising homogeneous, amorphous non-crystalline sialic acids having the following properties:

(a) broad absorption by differential scanning thermal analysis in the range of from about 165° C. to about 200° C. with substantially no heat absorption peaks in this temperature range, (b) a melting range of 131°–136° C. in a melting point measurement, and (c) a broad scanning angle (2θ) of 5°–40°, with no peaks, in an X-ray diffractionometric pattern.

2. A process for preparing an amorphous sialic acid powder comprising rapidly freezing an aqueous solution of sialic acids and freeze drying the frozen product, wherein said aqueous solution of sialic acids is frozen at a temperature below about −20° C. in about 0.01–900 seconds thereby preventing formation of crystal structures and forming homogeneous amorphous, non-crystalline sialic acids.

3. A homogeneous, amorphous, non-crystalline sialic acid composition produced by the process of claim 2.

4. A composition comprising homogeneous amorphous sialic acid, said composition being obtained by rapidly freezing an aqueous solution of sialic acids and freeze drying the frozen product under conditions sufficient to prevent formation of crystal structures thereby forming said homogeneous, amorphous sialic acids.

\* \* \* \* \*